US005865805A

United States Patent [19]
Ziemba

[11] Patent Number: 5,865,805
[45] Date of Patent: Feb. 2, 1999

[54] POWER INJECTOR AND SIDE LOADABLE SYRINGE SUPPORT THEREFOR FOR PLUNGER PUSHROD TYPE SYRINGES

[75] Inventor: Robert J. Ziemba, Cincinnati, Ohio

[73] Assignee: Liebel-Flarsheim Company, Cincinnati, Ohio

[21] Appl. No.: 895,155

[22] Filed: Jul. 16, 1997

[51] Int. Cl.[6] .................................................. A61M 37/00
[52] U.S. Cl. .......................................... 604/154; 604/218
[58] Field of Search ................................... 604/154, 155, 604/151, 131, 218

[56] References Cited

U.S. PATENT DOCUMENTS

| 5,279,569 | 1/1994 | Neer et al. | 604/154 |
|---|---|---|---|
| 5,451,211 | 9/1995 | Neer et al. | 604/218 X |
| 5,456,670 | 10/1995 | Neer et al. | 604/155 |

Primary Examiner—John D. Yasko
Attorney, Agent, or Firm—Wood, Herron & Evans L.L.P.

[57] ABSTRACT

A power injector is provided for injecting fluid from a replaceable syringe into the body of an animal. The syringe includes a syringe adapter interface for accepting side mountable syringes having pushrod extensions for actuating the syringe plungers from a point behind the syringe body. The injector is provided with an operator-removable and interchangeable interface in the form of a syringe mounting head. The interface includes a holder that has two halves, one fixed and one moveable, that open and close in a clam-shell fashion to respectively load or unload a syringe and to operate the syringe by driving the plunger thereof with a power driven ram that extends form the injector housing. The end of the injector ram, which is configured to normally couple to a button or key on the back of the plunger of a front or rear loadable syringe, is provided with an adapter that couples to the ram and to the large disk shaped end of a side loadable syringe pushrod. The adapter has opposed spring biased gripping fingers projecting forward of a coupling plate on the adapter in order to clip the pushrod end to the adapter. The fingers are configured and spaced relative to the coupling plate to engage the pushrod end either upon axial advancement against it or when the syringe is translated sideways into the holder.

11 Claims, 4 Drawing Sheets

POWER INJECTOR AND SIDE LOADABLE SYRINGE SUPPORT THEREFOR FOR PLUNGER PUSHROD TYPE SYRINGES

This invention relates to power injectors, and particularly to injectors for side loadable pushrod type syringes. More particularly, the present invention relates to the configuration of syringe support structure in power injectors, particularly that configured to primarily receive syringes of either the front or breach loadable type, and to the adaptation of such injectors to receive and use side loadable pushrod type syringes for purposes such as CT and angiographic applications.

BACKGROUND OF THE INVENTION

Power injectors are devices used to inject fluids at controlled or programmed rates or pressures into patients. Important uses include computed tomography (CT) and angiography, where a radiopaque contrast medium is injected into a patient's vascular system to enhance diagnostic images. With power injectors, a motor-driven ram advances the plunger of a syringe under microprocessor control to provide control of injection parameters such as flow rate, volume and timing. Such injectors are often loaded with sterile empty syringes with their plungers forward and that are filled by drawing fluid from a supply into the syringe through the syringe nozzle by using the ram to draw the syringe plunger backward. In other situations, the injectors are loaded with prefilled syringes. In either case, the syringes used are typically disposed of after a single use.

A variety of syringes have been developed and are in use as both prefilled and fillable syringes. Some such syringes are provided with pushrods extending rearwardly from the plunger and beyond the rearward end of the syringe body. Reasons for this may include the need to operate the syringe plungers by hand, where the plunger pushrod serves as a handle for the manual advance or retraction of the plunger, or may include a desire to couple the plunger to a drive ram at a point outside of the syringe body, even where the syringe is empty and the plunger is at the forward end of the syringe. In such cases, the plungers may be permanently connected to the pushrods in manufacture or once assembled, and will project behind the rear rims of the syringe bodies.

Many of such syringes are further provided with an outwardly projecting flange which serves to hold or support the syringe against axial motion so that force can be applied between the flange and the remote end of the pushrod to operate the syringe plunger. The remote end of the pushrod is usually provided with a flat surface against which force can be applied to advance the plunger, as well as outwardly extending edge or rim structure that can be hooked and pulled to enable the plunger to be retracted. Such a pushrod may, for example, be provided with a disk shaped remote end that is larger in diameter than the pushrod shift. When inserted into holders of injectors or other syringe operating devices, such syringes are most conveniently configured to be loaded into the syringe holders of the devices from the side. Widely used syringes of this type include 100 ml. and 200 ml. syringes manufactured by Nemoto of Japan.

Certain of the inventors of the subject matter of the present application have provided front loading injectors that are adapted to receive front loadable syringes. A front loading injector is one in which a front loadable syringe is positioned in front of an opening in an injector holder and loaded into the holder by translating the syringe rearwardly, back end first, into the injector. Such a front loading injector is described and illustrated in U.S. Pat. No. 5,279,569, which is assigned to the assignee of the present application, and is expressly incorporated by reference herein.

In addition, breach loading or rear loading injector holders are still provided for many applications. Rear loading injectors are injectors in which a rear loadable syringe is positioned behind a holder of the injector and translated, so structure on the syringe, usually a flange or other outwardly extending element at the syringe rear, seats forwardly against the holder. Usually the holder opens for loading or unloading of a syringe by pivoting away from the injector housing, either in hinged or turret fashion. One such injector is described and illustrated in U.S. Pat. No. 4,695,271, which is assigned to the assignee of the present application, and is expressly incorporated by reference herein.

Both rear and front loading power injectors are provided with rams that extend into the rear of a body of a syringe supported in the holder of the injector. The rams have coupling elements on the front ends thereof that engage structure on the rear of the plunger, within the body of the injector, often in such a way that the plunger can be both advanced and retracted by the motion of the ram. Where empty syringes are used and filled after loading on the injector, the rams of many front and rear loading injectors are of a diameter somewhat smaller than the internal diameter of the syringe, which minimizes the risk that the ram will contact the inside of the syringe body and contaminate the cavity before the plunger is retracted to fill the syringe.

With syringes that have plunger pushrods or rearward plunger extensions, their use with either rear loading or front loading injectors is difficult to achieve. Such syringes are not compatible with the ram-plunger coupling structure with which front and rear loading injectors are provided and the extension of the pushrod rearwardly of the back end of the syringe body interferes with a support of the syringe in a suitable position on the syringe holder of the injector. Such coupling structure often includes a button or key at the center of the rear wall of the plunger with a mating socket or set of jaws centered on the tip of the ram. Furthermore, providing special purpose injectors configured to handle side loadable syringes has not been regarded as practical in the prior art.

Accordingly, there is a need for a power injector that can make use of pushrod type syringes, particularly prefilled syringes, and particularly for injectors that can also be used with syringes of the front and rear loadable types.

SUMMARY OF THE INVENTION

A primary objective of the present invention is provide power injection for a pushrod type syringe, particularly for a syringe of the type in which a pushrod is connected to and extends rearwardly from the rear of the syringe body and terminates in a large actuator at its remote end. A particular objective of the present invention is provide an injector to receive a syringe of the pushrod type, side loadable.

A more particular objective of the present invention is to provide a power injector of a rear or front loading type with the capability of being loaded with and using a syringe of the side loadable type, particularly a syringe having a large diameter pushrod actuator extending from the rear of the syringe body, and more particularly where the syringe has flange or other outwardly extending mounting or locking structure at the rearward end of the syringe body. A specific objective of the present invention is to provide for the coupling of the plunger pushrod to the ram in which the ram is of small diameter and configured to normally extend into the back of the syringe body.

According to the principles of the present invention, a power injector is provided with a syringe holder for supporting a side loadable syringe thereon. Preferably, the holder has a stationary half that is fixed to a head and has a syringe receiving semi-cylindrical bore, and also has a moveable half that is pivotal, about an axially oriented axis on the side of the stationary half and also has a semi-cylindrical bore therein. The moveable half is preferably pivotal to a closed position at which the two bores define a semi-circular fully cylindrical bore or cavity within the holder to hold the rearward end of the body of a syringe. The moveable holder half is also preferably pivotal to an open position at which a syringe can be loaded and unloaded sideways to and from the holder.

In accordance with the preferred embodiment of the invention, the holder is mounted to a syringe mounting head and extends forwardly of the injector. The holder has syringe supporting structure thereon configured to engage a flange or other outwardly extending mounting structure on the rearward end of the syringe body, fixing the mounting structure at a distance forward of the housing with the body of the syringe extending forwardly from the holder. The syringe supporting structure preferably has a sidewardly facing slot therein configured to receive outwardly extending mounting structure on the rearward end of the syringe for the side loading of the syringe into the supporting structure of the holder.

In accordance with further principles of the invention, an interface is provided for adapting a front or rear loading power injector for use with a replaceable syringe which has a syringe body, a flange at the rear of the body a slidable plunger within the body, and a plunger pushrod that extends from the plunger to the outside of the syringe body behind the flange. The interface connects the plunger pushrod, which is connected to the rearward facing side of the syringe plunger, to a coupling member at the rearward end of the pushrod that is typically in the form of a disc or other a radially outwardly extending member that has a peripheral edge.

Preferably, the interface or adapter includes inwardly extending elements in the form of an opposed pair of inwardly spring-biased fingers extending forwardly from the coupling face, each having forward surfaces thereon configured to spread the fingers to engage the coupling member of a syringe when advanced forwardly thereagainst. The fingers preferably have tips spaced from the coupling face so as to form a flat space to receive the coupling member of a syringe when inserted edgewise therein. Preferably, the connector on the adapter is in the form of a rearwardly extending button having an enlarged tip that is smaller in diameter than a syringe of the size supportable by the syringe supporting structure.

In accordance with further embodiments of the invention, a syringe mounting head is provided that is pivotally connectable to the housing of a power injector, with the head having a syringe holder extending forwardly of the housing with syringe supporting structure thereon configured to engage the mounting structure on the rearward end of the body of the syringe. The configuration of the holder fixes the mounting structure at a distance forward of the housing so that the body of the syringe mounted therein extends forwardly from and in approximate axial alignment with the ram of the injector. The head preferably includes a medium thereon, coded to identify a syringe of the size supportable by the syringe supporting structure of the head, positioned to be read by a sensor on the housing. The syringe supporting structure preferably has a sidewardly facing slot therein configured to receive outwardly extending mounting structure on the rearward end of the syringe for the side loading of the syringe into the supporting structure of the holder.

These and other objectives of the present invention will be readily apparent from the following detailed description of the present invention in which:

DETAILED DESCRIPTION OF THE PREFERRED EMBODIMENTS

Figure 1:
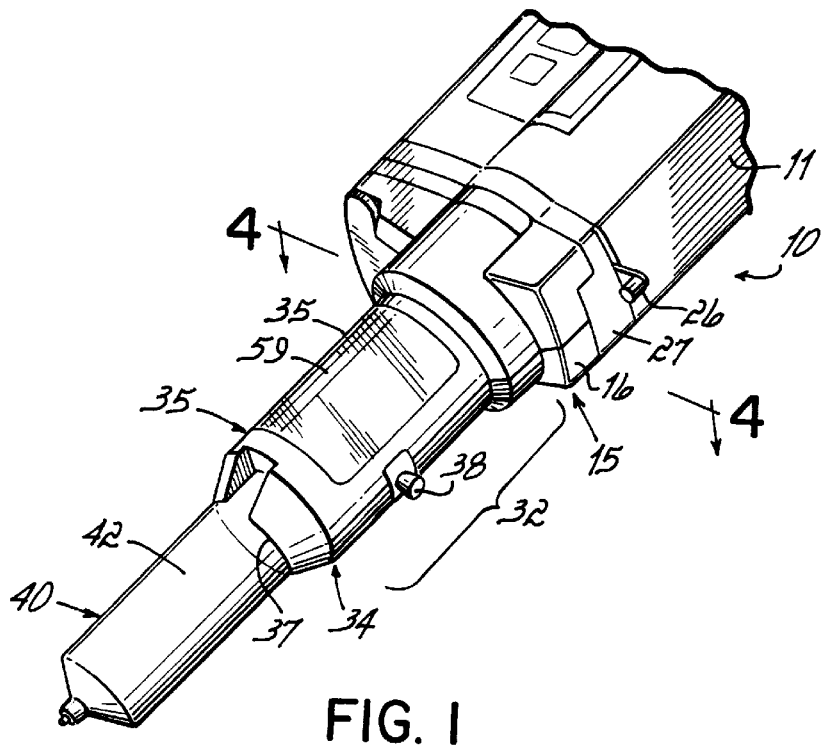
FIG. 1 is a perspective view of the front end of a power injector according to one preferred embodiment of the present invention, with a side loadable syringe supported therein and with the syringe holder thereof in a closed or operating position.
Figure 2:
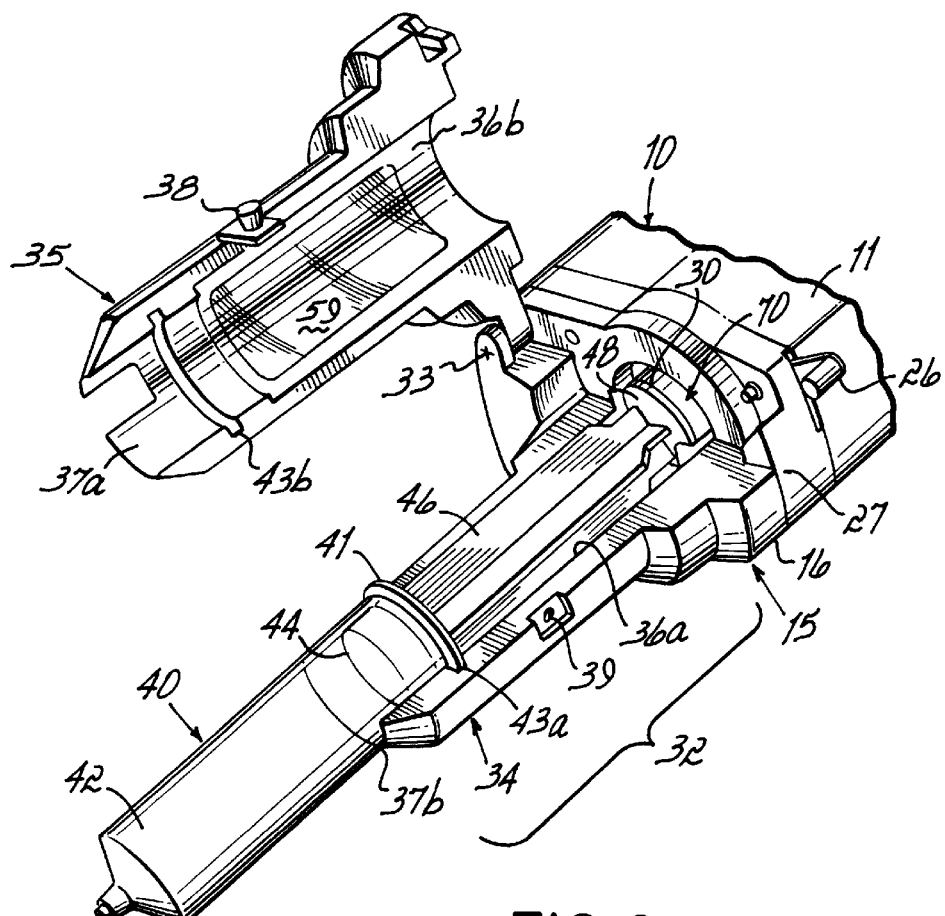
FIG. 2 is a perspective view similar to FIG. 1, illustrating the injector with the syringe holder in an open position for the loading and unloading of a syringe.
Figure 3:
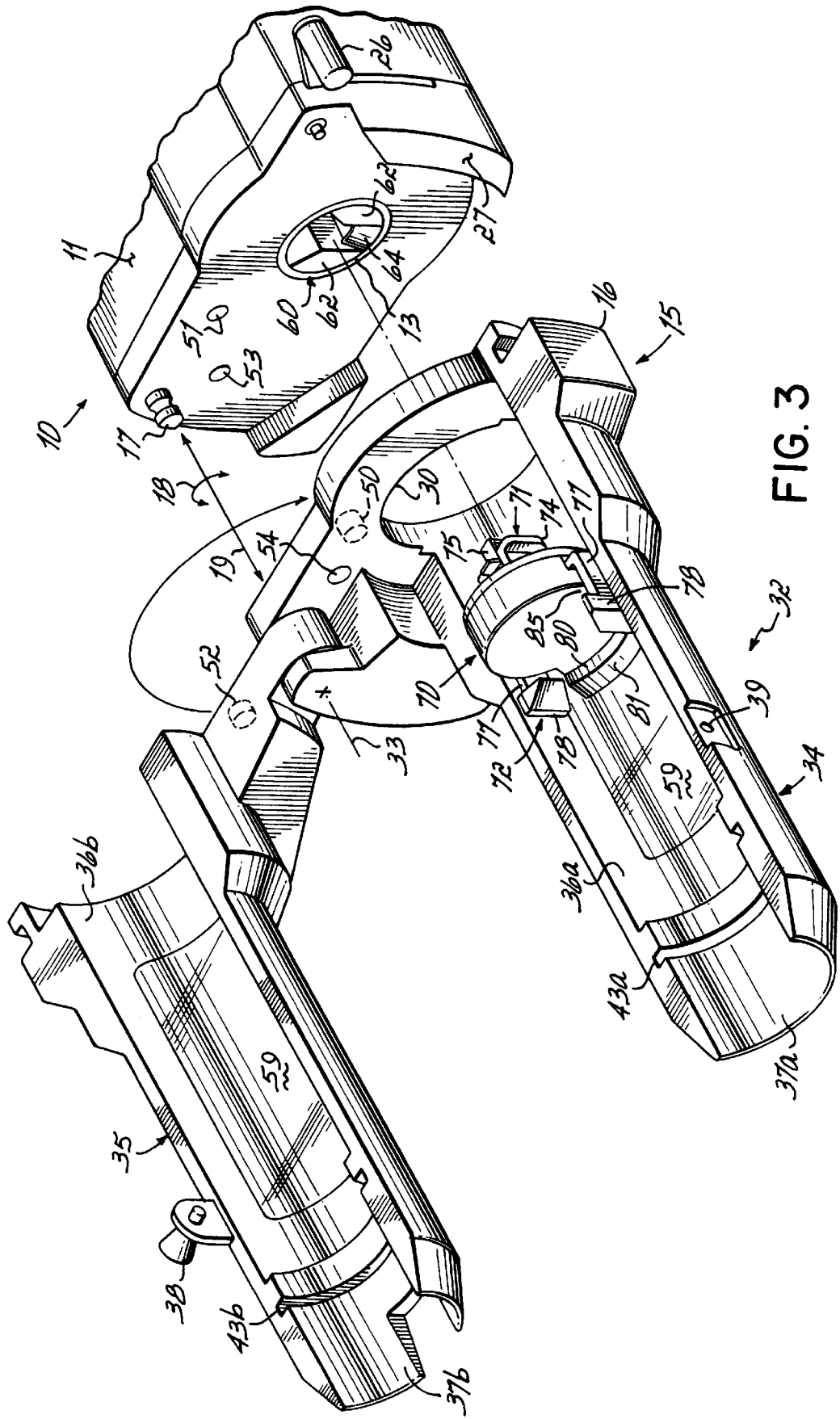
FIG. 3 is an enlarged view, similar to FIG. 2, of the injector with the holder in the open position but with the syringe removed.
Figure 4:
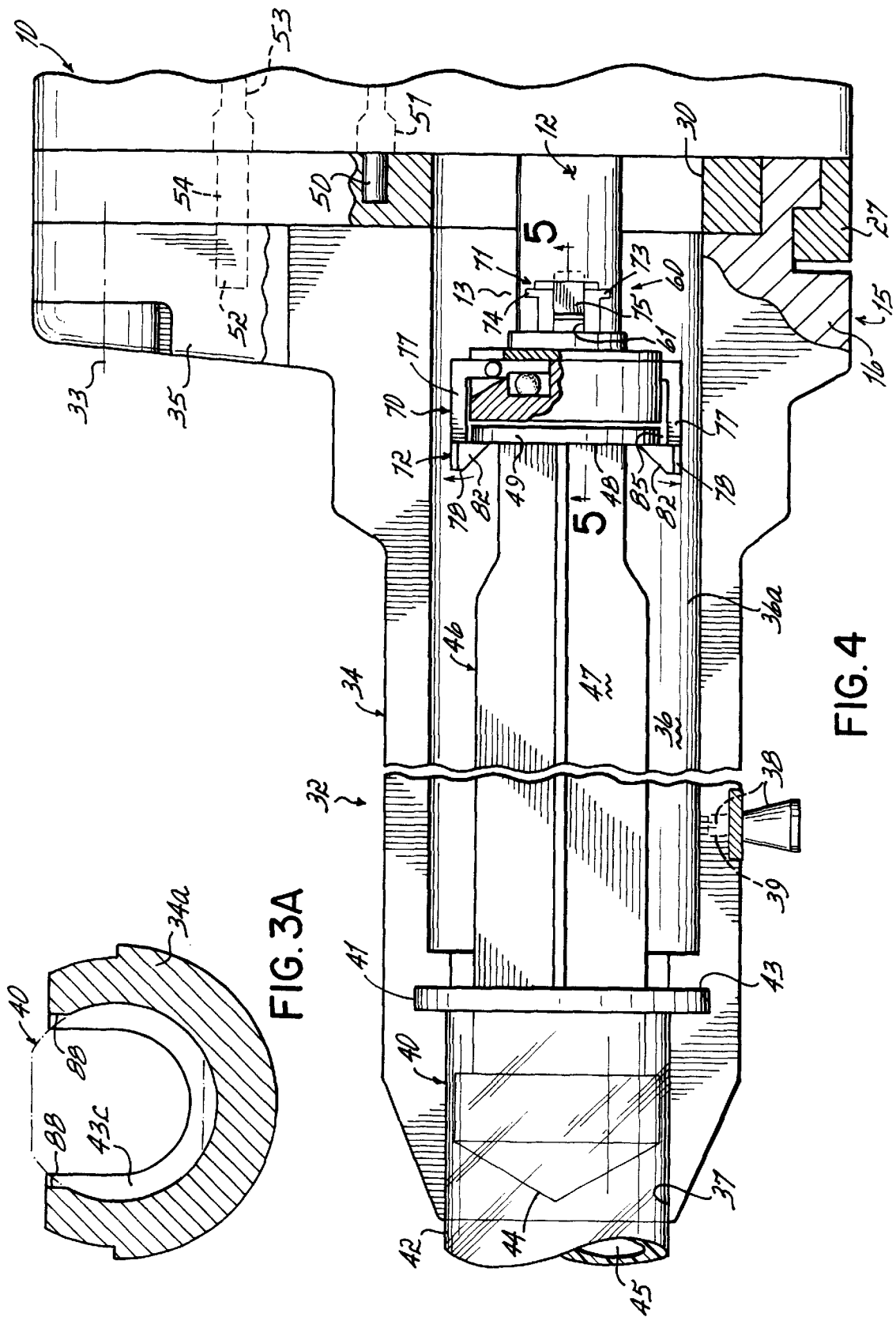
FIG. 4 is a cross-sectional view taken along the line 4—4 of FIG. 1.

FIGS. 1–4 illustrate the front end of a power head or injection module portion of a power injector 10 of a type, for example, that is used for angiographic and CT injection. One such injector is described and illustrated in U.S. Pat. No. 5,279,569, which is assigned to the assignee of the present invention, and is expressly incorporated herein by reference herein. The injector 10 includes an injector housing 11 that contains a power driven ram 12, as illustrated in FIG. 4. The ram 12 is longitudinally moveable by activation of a motor (not shown), contained in the housing 11, so that free end 13 of the ram 12 is extendable from a retracted position inside the housing 11, as illustrated in FIG. 3, to an extended position away from the housing 11, as more fully explained in incorporated U.S. Pat. No. 5,279,569. The injector of the incorporated patent is described therein as having a door assembly that constitutes a syringe mounting head of a front loading type, that is, of a type in which a syringe can be loaded by translating it rearwardly, back end first, into the front of the mounting head.

The embodiment of the invention illustrated in FIGS. 1–4 of this application is, however, equipped with a syringe mounting head 15 that is an alternative to the front loading head described in the incorporated patent. The mounting head 15 is rather of the side-loading type. The head 15 includes a mounting head base 16, which is pivotally connected to the front of the housing 11 to pivot, as illustrated by the arcuate arrow 18, about a longitudinal shaft 17 to pivot between a closed position, which is the position in which the head base 16 is illustrated in FIGS. 1, 2 and 4, slightly counter-clockwise to an open position in which the head 15 can be translated axially, as illustrated by the arrow 19, and removed, as illustrated in FIG. 3. In this way, the head 15 can be interchanged with the front loading head of U.S. Pat. No. 5,279,569.

The head 15 and housing 11 are provided with a locking mechanism (not shown), which has the function of locking and unlocking of the head 15 to and from the housing 11. The mechanism is provided with an operating lever 26 on the housing 11, illustrated in an unlocked position in FIG. 3, which is in the position which allows the head 16 to be opened, removed and replaced. The lever 26 is moveable to a locked position, illustrated in FIGS. 1 and 2. Movement of the lever 26 from its unlocked position to its locked position causes the head 16 to pivot downward into engagement with a latch 27, thereby securely locking the head 16 in its closed position. To perform the locking motion of the head 15, the locking mechanism may employ any suitable structure, but preferably employs the camming structure illustrated and described in detail in U.S. Pat. No. 5,279,569 referred to above. Such a mechanism may, for example, include a cam element (not shown) in the head 16 that is turned by a pin (not shown) linked to the lever 26 on the face of the housing 11.

The head base 16 has a generally circular opening 30 therethrough. With the lever 26 in this unlocked position, the center of the opening 30 is slightly to the side of, and out of alignment with, the centerline of the ram 12. When the head 15 is in its closed or locked position, the opening 30 is centered on and in alignment with the ram 12. Extending forwardly from the base 16 of the head 15 is a syringe holder 32. The holder 32 is formed in two parts, including a fixed part 34 and a moveable part 35 that is pivotally connected to the fixed part at a pivot shaft or axis 33. The shaft 33 is parallel to the ram 12 and to the side of the opening 30. The moveable part 35 of the holder 32 pivots on shaft 33 between a closed position, as illustrated in FIG. 1, which is its operating position, and an open position, as illustrated in FIG. 2, which is the position in which a syringe can be loaded into or removed from the holder 32. Preferably, each of the parts 34 and 35 of the holder 32 has therein a plastic window 59.

The holder 32, when closed, defines a cylindrical barrel 36, which may be considered as formed of two semi-cylindrical parts 36a and 36b, one in the fixed part 34 and one in moveable part 35, respectively, of the holder 32. The forward portion of the barrel 36 constitutes a cylindrical syringe receiving bore 37, also formed of two parts 37a, 37b. The two parts 34 and 35 of the holder 32 lock in a closed position by a spring-loaded hand-releasable lock 38 on the moveable holder part 35, which seats in a latch 39 on the fixed holder part 34, as shown in FIG. 4. The base 16 of the head 15 has a coded magnet element 50 therein which is detectable by a sensor 51 in the housing 11. The sensor 51 responds to the presence of the magnet 50 to provide information to controls in the housing 11 that the base 16 of the head 15 is locked in position on the housing 11. Similarly, a coded magnet element 52 is provided on the moveable part 35 of the holder 32 which is detectable through a port 54 in the base 16 by a sensor 53 in the housing 11. The sensor 53 responds to the presence of the magnet 52 to provide information to controls in the housing 11 that the moveable part 35 of the holder 32 is closed.

The holder 32 is configured to support a syringe 40 of a side loadable type having a rearwardly extending flange 41 at the rear end of a cylindrical syringe body 42. The diameter of the bore 37 is dimensioned to conform to the external diameter of the syringe body 42 of a syringe 40 of a given size and shape, such as a 100 cc or 200 cc syringe of the type manufactured and sold by Nemoto of Japan. To support such a syringe 40, the holder 32 is provided with an annular groove or slot 43 around the inside of the barrel 36, at a position near the forward end of the barrel 36 that defines the rearward end of the syringe holding bore 37. The slot 43 is in two semi-circular sections 43a, 43b, one section in each of the parts 34 and 35 of the holder 32.

When the moveable part 35 of the holder 32 is open, a syringe 40 can be inserted into or removed from the fixed part 34 of the holder 32, upon a transverse translatory motion of the syringe 40 relative to the fixed part 34 of the holder 32, with the flange 41 of the syringe 40 sliding into or out of the slot half 43a of the fixed part 34 of the holder 32. With the syringe 40 inserted in the fixed part 34 of the holder 32, the moveable part 35 of the holder 32 can be pivoted closed, bringing the slot half 43b into engagement with the remaining half of the flange 41 and closing the bore half 37b around the body 41 of the syringe 40. The body 41 of the syringe 40, so mounted in the holder 32, is spaced substantially forward of the housing 11, and the ram 12 of the injector 10 extends from and retracts into the housing 11 with the free end 13 thereof generally located somewhat rearwardly of the rear flange 41 of the syringe 40 whether the ram is retracted or extended.

Figure 3A:
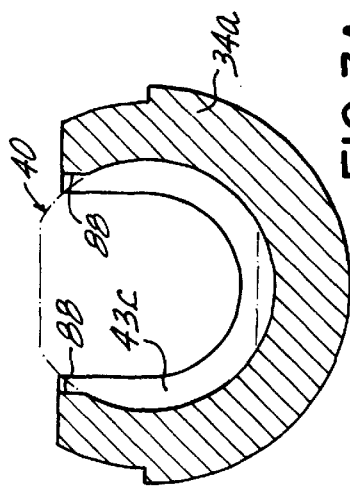
FIG. 3A is a cross-sectional view of the fixed part of the holder illustrating an alternative embodiment to that of FIGS. 1–3.

Alternatively, the fixed part 34 of the holder 32 may be made to circle a syringe by more than 180° in the vicinity of the slot 43, as illustrated in FIG. 3A. This is particularly advantageous where the syringe flange has parallel flats on its opposite sides. With such an embodiment, the body of the part 34 may extend and additional 30°–35°, for example, on each side, and the slot therein being in the form of slot 43c, configured at the two surfaces 88 at the upper edge to receive vertically oriented flat sides of the syringe flange, whereupon the syringe can be twisted up to a quarter turn to lock the flange in the slot 43c. This eliminates the need for a slot 43b in the moveable part 35 of the holder 32, simplifies the alignment thereof, and transfers more of the axial forces encountered during injection to the fixed part 34, which is structurally stronger.

Also, the holder 32 can be configured to provide a pressure sleeve to support a syringe held therein against outward expansion. To do so, the holder 32 may be dimensioned so that the bore 37 extends the entire length of the syringe 40 and at least partially around the front thereof, and the pivot shaft 33 can extend entirely along the side of the holder 32. Also, the lock 38 and latch 39 may be made of a type that securely fastens the two parts 34, 35 of the holder 32 in the closed position along the entire length of their adjoining surfaces on the side thereof opposite the shaft 33.

The syringe 40 has a stopper or plunger 44 slidably but sealably mounted within the body 42 to define the rear boundary of a fluid cavity 45 within the syringe body 42. Extending rearwardly from the plunger 44, either permanently or removably connected to the rearward facing side thereof, is a rearwardly extending plunger pushrod 46. The pushrod 46 has a shank 47 coaxially aligned with the body 42 of the syringe 40 which terminates at the rearward end thereof in a transverse disc shaped plate 48 having a radially outwardly extending rim or edge 49.

Figure 5:
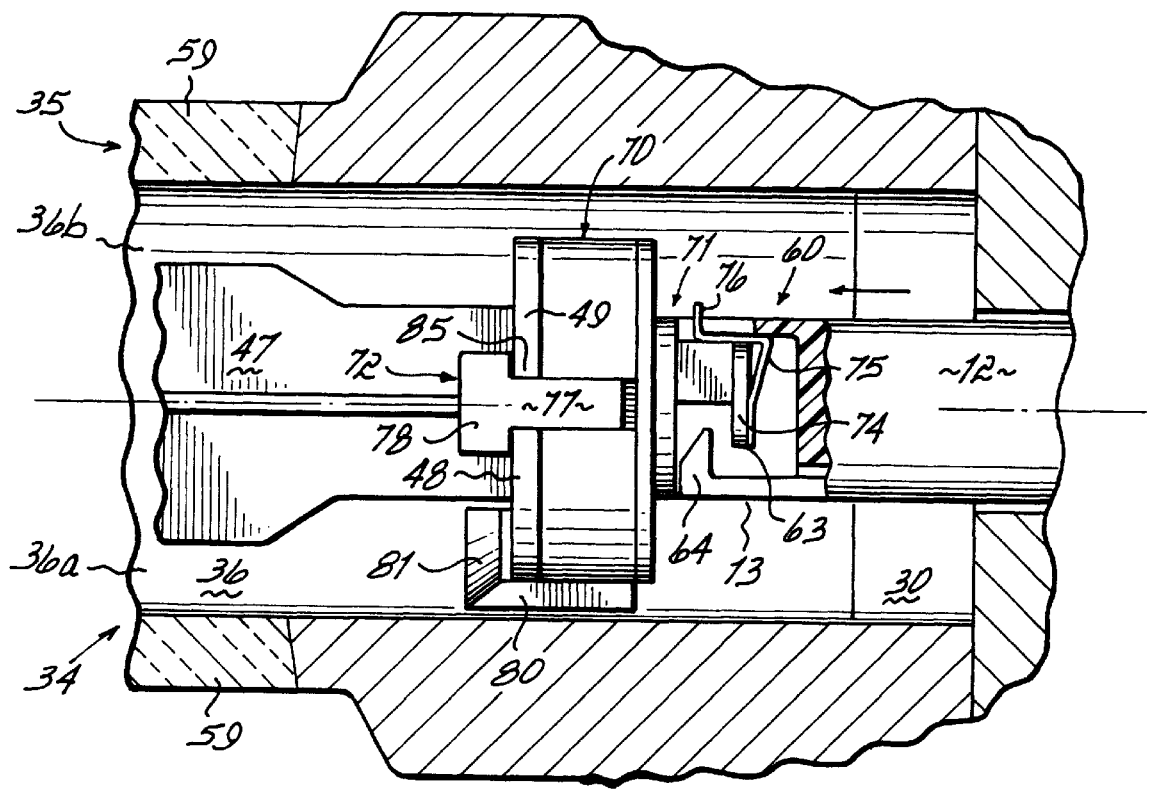
FIG. 5 is a cross-sectional view taken along the line 5—5 of FIG. 4.
Figure 6:
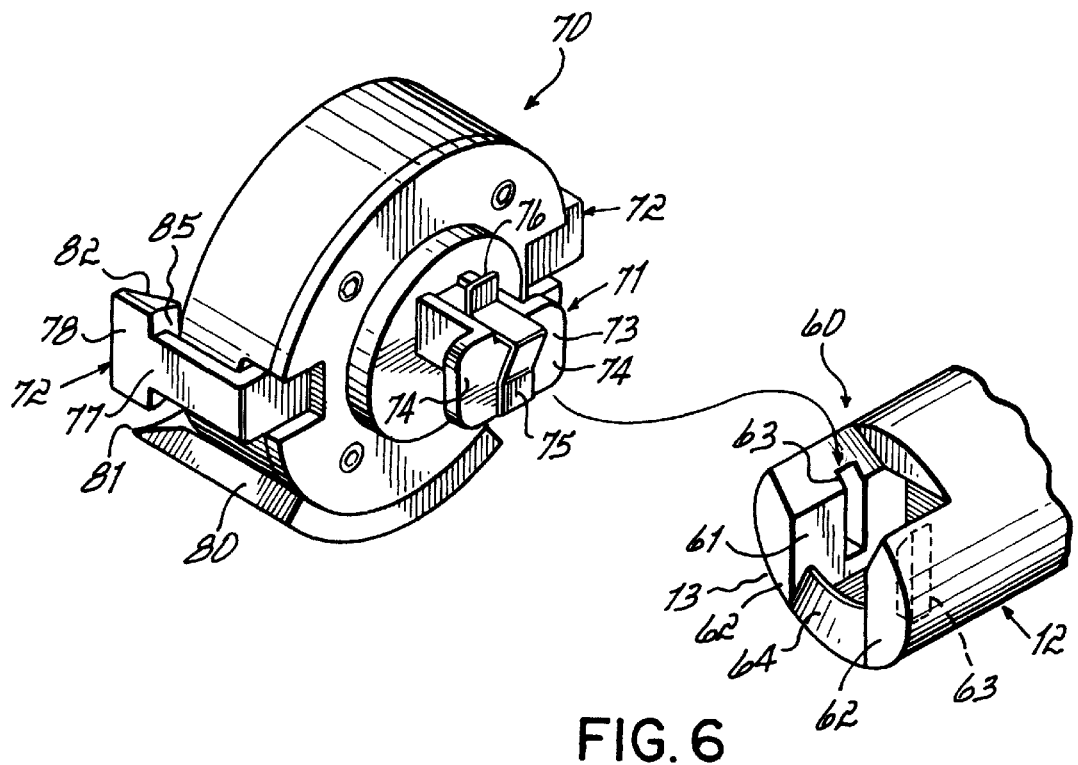
FIG. 6 is a disassembled perspective view, illustrating the ram coupling adapter of FIGS. 4 and 5.

The forward or remote end 13 of the ram 12, as illustrated in FIGS. 5 and 6, is provided with a connector 60 configured to receive a button type syringe plunger coupling of the type found on the syringe described in U.S. Pat. No. 5,279,569. The connector 60 may be of a type adapted to receive such a syringe plunger button only upon transverse relative movement of the button relative to the ram 12. Such a connector 60 preferably includes a pocket 61 between a pair of side portions 62 of the ram end 13, each with a vertical slot 63 on the inside thereof to receive the opposite edges of a plunger button only by transverse relative movement. Coupling and release of the button by relative axial movement of the ram 12 and plunger 44 is prevented by a lip 64 at the bottom of the pocket 61 that is fixed to the end 13 of the ram 12. Alternatively, the lip 64 at the ram end 13 may be made flexible in the radial direction with a tapered forward cam face, thereby providing a connector that is capable of coupling when the ram is advanced axially against the button of a plunger coupling, as illustrated and described in U.S. Pat. No. 5,279,569. In either form, the connector 60 will not connect to the disc 48 at the rearward end of the pushrod 46 in a manner that will allow the ram 12 to either push or pull the plunger 44.

To facilitate coupling between a ram 12 of the illustrated type and the rearward end of the pushrod 46, a coupling 70 is provided which serves as a ram-pushrod interface. The coupling 70 has a rearward half or ram coupling portion 71 for connection to the connector 60 at the remote end 13 of the ram 12, and a forward half or pushrod coupling portion 72 for connection to the disc 48 at the rearward end of the pushrod 46. The ram coupling portion 71 has a rearward extending button 73 thereon of generally T-shaped cross-section, which has a pair of outwardly extending edges or wings 74 that are configured to fit into the slots 63 of the connector 60. The button 73 slides into the connector 60 until it is in axial alignment with the ram 12, whereupon a spring clip 75 locks the button 73 into the ram 12. The spring clip 75 has a thumb release end 76 that permits the button 73 to be manually unlocked from the connector 60.

The pushrod coupling portion 72 of the coupling 70 has a pair of forwardly extending spring biased fingers 77 on the radially outward rim thereof, each with an inwardly hooked end 78. An arcuate guide member 80 is provided at the bottom of the pushrod coupling portion 72, having an outwardly flared forward edge 81. Similarly, the forward ends of the fingers 77 have outwardly flared surfaces 82. If the ram 12, with the coupling 70 attached, is advanced axially forward with a pushrod in the barrel 36, the disc 48 at the rearward end of the pushrod 46 will be cammed into axial alignment with the pushrod coupling portion 72 of the coupling 70, and the fingers 77 are moved radially outwardly as the disc 48 snaps into position between them, until it occupies a semicircular sidewardly facing slot 85 (FIG. 4). This is the preferred way of loading the syringe 14 in to the holder 32. The disc 48 can also be inserted into and removed from the slot 85 by being translated sideways relative to the coupling or interface 70. This would occur simultaneously with the insertion of the flange 41 of the syringe 40 into the slot 43a. The simultaneous sideways motion of the flange 41 and disc 48 is most convenient when removing the syringe 40.

The interface 70 adapts the ram of a front or rear loading power injector 10 for use with a replaceable syringe 40 which has syringe body 42 with an outwardly extending flange 41 that serves as syringe mounting structure at a rearward end of the body 42 for supporting the syringe against axial movement in the holder 32. The interface 70 connects the ram to a plunger 44 that is slidable in the body 42 and has pushrod 46 connected to the rearward facing side of the plunger 44 and projecting rearwardly beyond the rearward end of the body 42. The interface 70 clips to the disc shaped coupling member 48 at the rearward end of the pushrod 46 with the fingers 77 clipping around the outwardly extending edge 49 of the disc 48.

Those skilled in the art will appreciate that the applications of the present invention herein are varied, and that the invention is described in preferred embodiments. Accordingly, additions and modifications can be made to the embodiments of the invention illustrated and described herein without departing from the principles of the invention.

Therefore, what is claimed is:

1. A power injector for injecting fluid from a replaceable syringe and into the body of an animal, where the syringe has syringe body, outwardly extending mounting structure at a rearward end of the body for supporting the syringe against axial movement in a holder and a plunger slidable in the body and having a pushrod connected to the rearward facing side thereof and projecting rearwardly beyond the rearward end of the body with a coupling member at the rearward end thereof having a radially outwardly extending edge, the injector comprising:

a housing;

a power driven ram supported for reciprocal longitudinal movement on the housing and having a plunger coupling at the center of a free end thereof;

a syringe mounting head supported on the housing and having a syringe holder extending forwardly of the housing with syringe supporting structure thereon configured to engage the mounting structure on the rearward end of the body of the syringe to fix the mounting structure at a distance forward of the housing with the body of the syringe extending forwardly therefrom in approximate axial alignment with the ram;

an adaptor having a connector on a rearward side thereof that is removably connectable to the plunger coupling at the free end of the ram, the adapter having a radially outwardly extending coupling face on the forward side thereof, the coupling face having radially inwardly extending elements spaced forwardly of the coupling face and positionable around the radially outwardly extending edge of the coupling member on the rearward end of the pushrod to grip a forward facing side of the coupling member of a syringe and hold the coupling member between the coupling face and the clipping elements to drive the plunger forwardly and rearwardly with the ram.

2. The injector of claim 1 wherein:

the inwardly extending elements are in the form of an opposed pair of inwardly spring-biased clips extending forwardly from the coupling face, each having forward surfaces thereon configured to spread the fingers to engage the coupling member of a syringe when advanced forwardly there against.

3. The injector of claim 2 wherein:

the fingers have tips spaced from the coupling face so as to form a flat space to receive coupling member of a syringe when inserted edgewise therein.

4. The injector of claim 1 wherein:

the connector on the adapter is in the form of a rearwardly extending button having an enlarged tip that is smaller in diameter than a syringe of the size supportable by the syringe supporting structure.

5. The injector of claim 1 wherein:

the head includes a medium thereon coded to identify a syringe of the size supportable by the syringe supporting structure of the head, and the housing includes a sensor operable to generate a signal in response to the coded medium and a control responsive to the signal from the sensor to operate the ram in accordance with size of a syringe held by the syringe supporting structure.

6. The injector of claim 1 wherein:

the syringe supporting structure has a sidewardly facing slot therein configured to receive outwardly extending mounting structure on the rearward end of the syringe for the side loading of the syringe into the supporting structure of the holder.

7. The injector of claim 1 wherein:

the holder includes a stationary half fixed to the head and having a syringe receiving semi-cylindrical bore therein, and a moveable half pivotal about an axially oriented axis on the side of the stationary half and also having a semi-cylindrical bore therein, the moveable half being pivotal to a closed position at which the two bores define a cylindrical cavity within the holder and an open position at which a syringe can be loaded and unloaded sideways to and from the holder.

8. An ram adapter for adapting a front or rear loading power injector for use with a replaceable syringe which has a syringe body, a plunger slidable in the body and a pushrod connected to the rearward facing side of the plunger and projecting rearwardly beyond the rearward end of the syringe body, the pushrod having a coupling member at the rearward end thereof having a radially outwardly extending edge, where the injector has a housing and a power driven ram supported for reciprocal longitudinal movement on the housing and having a plunger coupling at the center of a free end thereof for interconnecting to the plunger of a front or rear loadable syringe and reciprocating the plunger in the syringe body with the ram extended into the body of a front or rear loadable syringe, the ram adapter comprising:

a connector forming a rearward side thereof, the connector being removably connectable to the plunger coupling at the free end of the ram;

a radially outwardly extending coupling face forming a forward side thereof, the coupling face having radially inwardly extending elements spaced forwardly of the coupling face and positionable around the radially outwardly extending edge of the coupling member on the rearward end of the pushrod to grip a forward facing side of the coupling member of a syringe and hold the coupling member between the coupling face and the clipping elements to drive the plunger forwardly.

9. The adapter of claim 8 wherein:

the inwardly extending elements are in the form of an opposed pair of inwardly spring-biased clips extending forwardly from the coupling face, each having forward surfaces thereon configured to spread the fingers to engage the coupling member of a syringe when advanced forwardly there against.

10. The adapter of claim 9 wherein:

the fingers have tips spaced from the coupling face so as to form a flat space to receive coupling member of a syringe when inserted edgewise therein.

11. The adapter of claim 8 wherein:

the connector on the adapter is in the form of a rearwardly extending button having an enlarged tip that is smaller in diameter than a syringe of the size supportable by the syringe supporting structure.

\* \* \* \* \*